US006399341B1

(12) United States Patent
Stegemann et al.

(10) Patent No.: US 6,399,341 B1
(45) Date of Patent: Jun. 4, 2002

(54) ARTIFICIAL PANCREAS

(76) Inventors: Jan Philip Stegemann, 599 Cambridge St., #402, Cambridge, MA (US) 02141; John Joseph O'Neil, 20 Leonard Dr., Marlboro, MA (US) 01752; Claudy Jean Paul Mullon, 163 Prospect St., Framingham, MA (US) 01701

( * ) Notice: Subject to any disclaimer, the term of this patent is extended or adjusted under 35 U.S.C. 154(b) by 0 days.

(21) Appl. No.: 09/431,981

(22) Filed: Nov. 2, 1999

Related U.S. Application Data

(62) Division of application No. 08/957,146, filed on Oct. 24, 1997, now Pat. No. 6,023,009, which is a continuation of application No. 08/606,422, filed on Feb. 23, 1996, now abandoned.

(51) Int. Cl.[7] ............................................. C12N 11/10
(52) U.S. Cl. ..................... 435/178; 435/177; 435/382; 424/424
(58) Field of Search ................................ 435/382, 177, 435/178; 424/424

(56) References Cited

U.S. PATENT DOCUMENTS

| | | | | |
|---|---|---|---|---|
| 3,959,251 A | * | 5/1976 | Porath et al. | |
| 4,391,909 A | * | 7/1983 | Lim | |
| 5,053,332 A | * | 10/1991 | Cook et al. | |
| 5,286,495 A | * | 2/1994 | Batich et al. | |
| 5,531,997 A | * | 7/1996 | Cochrum | |
| 5,643,569 A | * | 7/1997 | Jain et al. | |

OTHER PUBLICATIONS

Sun, A.M., Microencapsulation of pancreatic islet cells: A bioartificial endocrine pancreas (1988) Methods of Enzymology, vol. 137, pp. 575–580.*

Iwata et al., Agarose for a bioartificial pancreas (1992) Journal of Biomedical Materials Research, vol. 26, pp. 967–977.*

* cited by examiner

Primary Examiner—Jon P. Weber
Assistant Examiner—Harry J Guttman
(74) Attorney, Agent, or Firm—Law Offices of Margit Maus and Associates

(57) ABSTRACT

An artificial pancreas is described herein which comprises one or more viable and physiologically active pancreatic islet cells capable of producing insulin, encapsulated within a semipermeable spheroidal membrane comprising agar gel. Further disclosed are a method for producing agar microbeads, a tissue implantation method and a reseeding method for the artificial pancreas.

7 Claims, 1 Drawing Sheet

ARTIFICIAL PANCREAS

This application is a divisional of Ser. No. 08/957,146 filed Oct. 24, 1997 now U.S. Pat. No. 6,023,009 which is a continuation of Ser. No. 08/606,422 filed Feb. 23, 1996 now abandoned.

BACKGROUND OF THE INVENTION

This invention relates in general to artificial organs and more specifically to an artificial pancreas device comprising agar microbeads.

The prior art while replete with encapsulation techniques is still devoid of an encapsulation technique which mimicks the function of the in vivo organ intended to be replaced. Thus in the case of insulin delivery, the existing encapsulation techniques employ pancreatic islet cells encapsulated in an alginate semipermeable membrane. The drawback of such techniques is as follows.

First, alginate gels by an ionic mechanism. The polymer-reacts with di- or trivalent cations in such a way that the polymer structure becomes ionically cross-linked and forms a gel structure. The gels thus formed are thermally stable, but because of their ionic nature can be destabilized by substances which sequester the cross-linking ions.

Second, alginate beads are usually further processed by coating with poly-L lysine to produce a semi-permeable shell around the alginate itself for immunoisolation of the encapsulated material. In most cases the alginate core is then dissolved so that the alginate beads actually end up as poly-L-lysine capsules. The use of poly-L-lysine has been shown, however, to cause severe aggregation and clumping of the beads which cause the cells to stop functioning. Moreover, poly-L-lysine is itself reactive leading to immunological rejection and bioincompatibiliy which results in host rejection and fibrotic overgrowth and unwanted bead aggregation leading to decreased cell function.

Third alginate beads are potentially dissolvable in environments which contain substances which sequester calcium or barium.

Fourth, alginate beads have been reported to elicit unwanted biological responses, most notably cytokine release and fibrotic growth. Notably, there is an ongoing debate whether these responses are caused by the alginate itself, the particular type of alginate, the coating poly-L-lysine as noted above or some other factor.

Fifth, the long term stability of alginate beads aside from the aforementioned problems, has been called into question.

Lastly, implanted alginate beads are not retrievable once they stop functioning or start leading to adverse clinical effects.

Therefore, a need still exists for a method to encapsulate viable pancreatic cells which allows for the production of insulin while guarding against the host's immune system.

SUMMARY OF THE INVENTION

The aforementioned need is met in an elegant and novel manner by providing for an artificial pancreas comprising one or more viable and physiologically active pancreatic islet cells capable of producing insulin, encapsulated within a semipermeable spheroidal membrane comprising agar gel. Said artificial pancreas may be installed within a diffusion chamber or perfusion chamber containing a hollow fiber.

The present invention further provides for an encapsulation process comprising the steps of suspending islet cells in molten agar and emulsifying said solution in a hydrophobic phase to form an emulsion of small liquid droplets suspended in hydrophobic phase. Cooling of the oil thereafter causes the droplets to gel resulting in the formation of agar gel microbeads.

Lastly the present invention provides for a tissue implantation method comprising the aforementioned encapsulation steps followed by introducing said encapsulated beads into a mammalian body.

DETAILED DESCRIPTION OF THE INVENTION

Figure 1:
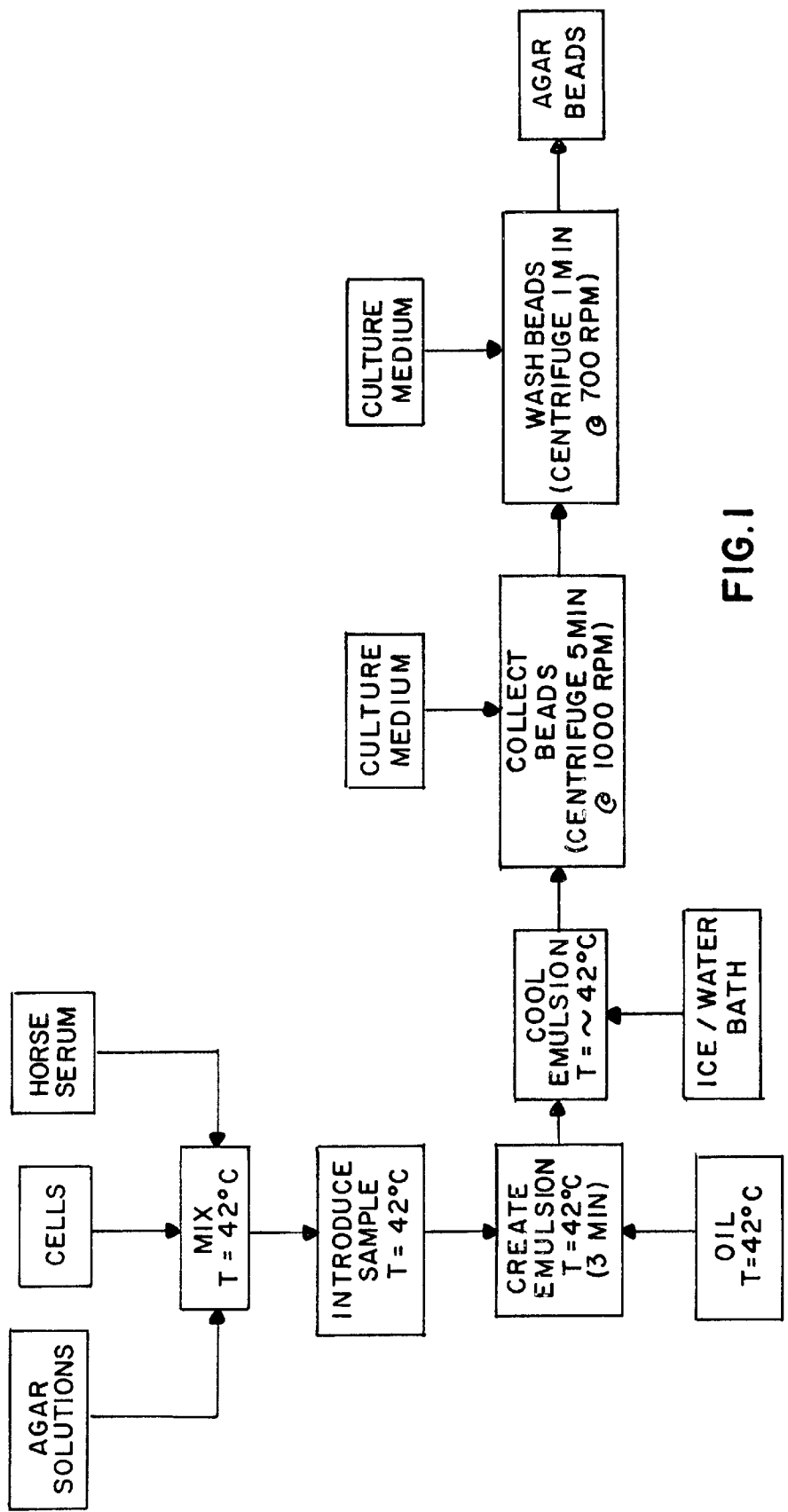
FIG. 1 depicts a schematic view of the novel agar microbead encapsulation process.

The present invention diverts from the prior art in one main aspect, namely that it employs agar as opposed to alginate beads. The present invention contemplates all the different kinds or grades of agar ranging from pure i.e. agarose to impure kinds. The different types of agar differ from one another by their gelling temperature and resultant gel strength. When extracted from seaweed agar consists of a gelling fraction, agarose, and a non-gelling fraction, agaropectin, with other impurities mixed in. Further processing may then be performed to separate, extract or purify the agar i.e. to separate the agarose from the agaropectin and other impurities. The present invention encompasses all agar type and is not limited by gelling temperature or gel strength.

Not only do agar beads overcome the problems of the prior art as previously noted, but they bring about numerous advantages among them the following.

Agar gels by a thermal mechanism as opposed to the ionic one of alginate beads. This difference imparts chemical stability to agar beads in that they do not dissolve in certain ionic solutions. The aforementioned difference also imparts thermal stability in that cooling of a heated solution of agar in water causes helical coil segments of the polymer to intertwine and to eventually form a three-dimensional gel structure. And the very particular three dimensional structure imparts the advantageous property of hysteresis i.e. when the melting temperature is considerably higher than the gelling temperature. Thus cells can be put into solution at approximately 40 degrees Celsius, and the solution will not gel until below 37 degrees Celsius or melt until above approximately 80 degrees Celsius. Thus the agar environment is chemically more stable than alginate.

The novel encapsulation process of the present invention in general comprises the steps of suspending islet cells in molten agar and emulsifying said solution in a hydrophobic phase to form an emulsion of small liquid droplets suspended in hydrophobic phase. Cooling of the oil then causes the droplets to gel resulting in the formation of agar gel microbeads. In this form the agar microbeads can be readily collected from the hydrophobic phase and washed. This process advantageously allows for the production of relatively large quantities of relatively large gel beads. By way of illustration and not limitation the novel process yields from about 5 to about 50 mL microbeads ranging from about 50 to about 1000 microns in diameter.

This novel process is schematically depicted in FIG. 1. First an agar solution, pancreatic islet cells and preferably but not necessarily, surfactant are mixed. The agar is heated to above 80 degrees Celsius until it melts but is cooled to from about 35 to about 45 degrees Celsius before the islets are added. The resultant mixture of agar, cells and optionally surfactant is added to a hydrophobic phase. The hydrophobic phase temperature has to be warm enough to maintain the agar mixture as a liquid while it is being emulsified but not so hot as to damage the cells. The preferred temperature range in the current process is from about 42 to about 43 degrees Celsius. The resultant mixture is emulsified and cooled. Any emulsification medium may be employed so long as the emulsification and the sample to be made into beads are not miscible. By way of illustration and not limitation mention may be made of silicone fluid, vegetable oils, mineral oils, etc. Among silicone fluids polydimethylsiloxane is most preferred. Emulsification is obtained by dropping the temperature below the gelling point of agar, quantitatively speaking this is from about 35 to about 39 degrees Celsius for impure agar and from about 8 to about 42 degrees Celsius for pure agar i.e. agarose. The current process limits the time of exposure of the cells to the silicone fluid since it contains no nutrients such as oxygen to sustain the cells to about 10 to 30 minutes. The emulsion is cooled to about 1–10 degrees Celsius. Next the beads are collected and washed. The beads are centrifuged at a speed sufficient to separate the gelled beads from the oil phase. This is preferably done as quick as possible to minimize the time the cells are out of their nutrient medium. Thus by way of illustration and not limitation, we contemplate speeds ranging from about 700 to about 1500 rpm for from about 2 to about 10 minutes. The particular speed and time will depend on the size of the centrifuge tubes to be used and the size of the beads to be produced. During the collection and washing phase culture medium may be added.

Specifically the novel encapsulation process comprises the following preparatory steps. First a 1–3% tissue culture grade agar solution is prepared by dissolving sterile agar powder in hot sterile water. The resultant agar solution is diluted by 50% with a double concentration culture medium and is kept at approximately 42 degrees Celsius until used. Alternatively, the agar solution can be made up in medium so long as the agar solution is isotonic so that it does not kill the cells. An emulsification medium is sterile filtered and prewarmed in a water bath to about 42–43 degrees Celsius. By way of illustration and not limitation emulsification mediums may comprise silicone, mineral or vegetable oil, etc.

The pancreatic cells to be entrapped in the agar beads are collected and centrifuged to form a compact tissue pellet. Notably, the present invention contemplates any cell type for encapsulation and does not restrict the invention to the use of the following cell types: pancreatic islets, hepatocytes, dopamine-secreting cells, antibody secreting cells, hybridoma cells and other cell types capable of secreting therapeutic agents.

Any physiologically tolerable surfactant may be used to encapsulate the cells i.e. to promote the break-up of droplets in the emulsification step. Specifically any type of serum may be used yet heat inactivated horse and fetal bovine serum are most preferred. If surfactant is used it should be kept at about 42 degrees Celsius before use.

An ice bath is prepared and kept ready. Similarly a culture medium or isotonic saline is kept available at room temperature for use in the bead washing step. By way of illustration and not limitation the following culture mediums may be mentioned: saline, Minimum Essential Medium, Dulbecco's Modified Eagle Medium, Medium 199, Roswell Park Memorial Institute medium, Krebs/Ringers solution, etc.; all described in JRH Biosciences' Inc. catalog entitled: "Catalog and Handbook for Cell Culture Scientist." Most preferred are isotonic saline and alpha Minimum Essential Medium also as described in the above referenced catalogue.

Regarding the equipment, an impeller and preferably a two bladed impeller, is used to create an appropriate flow field for the emulsification of the liquid agar while preventing entrainment of air. With the preferred two bladed impeller, two blades are mounted on an impeller shaft at right angles to each other such that one impeller is at the end of the shaft and the other is at a distance of about one-half the impeller length above the first impeller. Since it is preferred that the impeller assembly be sterilized prior to use, it is recommended that a stainless steel drive shaft and autoclavable impeller blades be used.

The invention further contemplates the use of a mixer with good speed control ranging from about 60 to about 2300 RPM, preferably from about 380 to about 800 rpm to drive the impeller. Preferably said mixer will also have a digital RPM display. The mixer head is preferably mounted vertically on a sturdy retort stand.

An emulsification vessel approximately 1.5–2.0 times the diameter of the impeller blade is recommended. A vessel 3–4 cm larger in diameter than the emulsification vessel is recommended for the ice/water bath. Both vessels are preferably mounted on the same retort stand as the mixer head with ring clamps. In this manner, the impeller can be moved into the emulsification vessel and the ice/water bath can subsequently be moved to surround the emulsification vessel.

Turning now to the encapsulation procedure itself, it is preferably carried out under sterile conditions. To that end all pieces of equipment should be sterilized and standard aseptic techniques should be applied when handling cells, equipment and reagent.

The emulsification medium is transferred to an emulsification vessel while at 42 degrees Celsius. The impeller assembly is lowered into the oil phase such that there is sufficient clearance from the surface of the oil to prevent entrainment of air and about 1–1.5 cm clearance from the vessel bottom. Impeller rotation is initiated. Rotation is set from about 380 to about 800 RPM and a steady flow pattern is allowed to develop. The cells to be embedded are mixed with from about 5 to about 50 mL of molten agar at 42 degrees Celsius. Serum ranging from about 0 to about 20%, 20% being most preferred, is added as a surfactant. The resultant liquid agar/cell suspension is allowed to form an emulsion. Once a homogeneous emulsion is obtained, the ice/water bath is secured around the emulsification vessel such that the entire oil phase is immersed. The emulsion vessel is thereafter cooled for about 10–20 minutes or qualitatively speaking, until the agar/cell droplets have formed solid gel beads. Once the beads have gelled, the speed of the impeller rotation may but does not have to be decreased to about 300 RPM during the cooling period when stable but not fully gelled beads are formed to prevent shear damage to cells or beads. Once the beads are fully gelled, the impeller is stopped and removed from the emulsification vessel.

The oil and agar/cell suspension is decanted into a centrifuge tube and a volume from about 25 to about 75% of the total suspension volume of culture medium or isotonic saline is added. The suspension is thereafter centrifuged until the aqueous phase is separated from the oil phase, qualitatively speaking, for about 3 to 5 minutes at from about 800 to about 1000 RPM. Since the beads will be concentrated in the aqueous phase at the bottom of the centrifuge tube, they can be collected by pipet. The beads are thereafter washed several more times by repeated dilution with culture medium or saline and centrifuged from about 2 minutes to about 4 minutes at from about 500 to about 1000 RPM. The resultant washed beads are ready for use in in vivo or vitro applications.

The aforementioned procedure produces spherical agar beads containing viable cells. The size and size distribution of the beads may be controlled by controlling the following operating parameters: rate of impeller rotation, impeller and vessel geometry, hydrophobic phase and viscosity, agar concentration and viscosity, surfactant concentration, temperature/time protocol, etc. Thus for instance a faster rotation will give smaller beads with a narrower size distribution while a slower rotation gives larger beads. Impeller and vessel geometry are important to minimize high shear areas since shear forces can damage cells. A double bladed impeller is preferred since it prevents the entrainment of air into the emulsion. Round vessels are also preferred since they minimize shear areas. The ratio of the impeller diameter to vessel diameter is important to ensure proper flow pattern. The agar concentration and type will determine the strength and permselective properties of the resulting beads. Moreover the agar concentration will determine the viscosity which affects how easily the agar breaks up into discrete droplets in the emulsion. Surfactant lessens the surface tension of the liquid agar thus promoting the break up into discrete droplets. The higher the concentration of surfactant the more easily the droplets form up to a certain point above which increasing the surfactant concentration has no effect. The temperature and time parameters are important to ensure the survival of the cells through the encapsulation process. The temperature used will determine the time necessary to cool the emulsion below the gelling temperature of the agar. The aforementioned are but a few of the many well known factors in the art to be considered when controlling the operating parameters.

The most widely used size of agar bead for embedding of cells for use in artificial organs or drug delivery devices is in the range of from about 50 to about 1000 um in diameter. The aforementioned process consistently produces beads in this range.

Beads harvested by the aforementioned process may be implanted directly via injection into a mammalian body or may be further encapsulated in an immunoisolating membrane. Depending on whether the beads are to be directly implanted or further encapsulated in a membrane, different immunoisolating precautions are required. If the beads are to be directly implanted, the gels molecular weight cut-off needs to be controlled unless immunosuppression therapy is used. If immunosuppression therapy is not used, a molecular weight cut-off below 100,000 daltons is preferred to fend off immune attacks. This molecular weight control is accomplished by controlling the concentration of agar used to make the beads. A higher concentration gives a tighter membrane. The present invention contemplates agar concentrations ranging from about 0.2 to about 5.0% weight by volume. Notably, beads made of a lower agar concentration can be coated again with agar of a higher concentration to mimick a capsule surrounded by a permselective membrane. If so, the outer coating should fall within the aforementioned agar concentration range.

If the agar microbeads are intended to be further encapsulated in an immunoisolating membrane, then the immune response is controlled by the properties of the second membrane i.e. the molecular weight cut-off of the beads is not limited to 100,000 daltons but can be higher or lower. By way of illustration and not limitation mention may be made of the following immunoisolating membranes: mechanical membranes, for example having straw or pouch configurations; synthetic membranes such as polyacrylonitrile/ polyvinylchloride, polysulfone, cellulose acetate, hydroxyethylmethacrylate/methylmethacrylate, etc. When injected into a mechanical device such as a diffusion chamber or a perfusion chamber, the device is surgically implanted into the body. Notably seeding may occur before or after implantation of the device.

While the present invention is not restricted to any one device, applicant particularly contemplates diffusion, perfusion and perfusion/ultrafiltration devices. By diffusion devices applicant contemplates a device comprising agar beads contained within a semipermeable membrane which when implanted in a body is in contact with body tissue to enable insulin, glucose and nutrient transport by diffusion. Said membranes may be in a straw, disk,pouch, etc. configuration. More specifically, reference may be made for illustrative and not a limiting purpose to the devices described in the following articles, said articles hereby incorporated by reference: Lanza R P, Sullivan S J, Chick W I, "Islet transplantation with immunoisolation", Diabetes, 41, 1503–1510, 1992.; Gu Y J, Inoue K, Shinohara S, Doi R, Kogire M, Aung T, Sumi S, Imamura M, Fujisato T, Maetani S, Ikada Y, "Xenotransplantation of bioartificial pancreas using a mesh-reinforced polyvinyl alcohol bag", Cell Transplantation, 3(Supp.1) S 19-S 21, 1994; Aung F, Kogire M, Inoue K, Fujisato T, Gu Y, Burczak K, Shinohara S, Mitsuo M, Maetani S, Ikada Y, Tobe T. "Insulin release from a bioartificial pancreas using a mesh reinforced polyvinyl alcohol hydrogel tube", ASAIO Journal, 39, 93–96, 1993; Colton C K, "Implantable biohybrid artificial organs", Cell Transplantation, 4 (4), 415–436, 1995; and Hill R S, Scharp D W, Johnson R C, Neueunfeldt S, Hager S R, Hegre O D, Lacy P E, "Reversal of diabetes in the mouse following transplantation of macroencapsulated xenogeneic rat islets", Fifth International Congress on Pancreas and Islet Transplantation Abstracts, P.93, 1995.

Exemplary perfusion devices contemplated by applicant consist of a membrane inside an acrylic housing. Blood flows axially through the membrane and insulin is secreted by islets radially through the membrane into the blood. The perfusion/ultrafiltration device is a modification of the perfusion device which comprises added membrane openings or windows in the device housing which allow for the diffusion of insulin out of the device into the peritoneum.

A particular example of a perfusion device is applicant's copending patent application Ser. No. 08/488,033 entitled "Novel Artificial Pancreas", hereby incorporated by reference, offers particular applicability. Said artificial pancreatic perfusion device comprises a hollow fiber having a porosity or molecular weight cut off ranging from about 20,000 Dalton to about 200,000 Dalton. The hollow fiber has one end connected to a blood vessel for receiving blood and a second end connected to a blood vessel for returning said blood to the patient. Pancreatic islet cells are seeded around the hollow fiber. The fiber and islets are enclosed in an acrylic housing having a pore size small enough to offer protection to the islets and host from immune reactive substances.

In use, the novel pancreatic perfusion device allows for ultrafiltration and convection transport. The hollow fiber providing for ultrafiltration and the semipermeable housing providing for convection. Thus blood flow through the hollow fiber assures a steady supply of nutrients to the islets while fluid perfuses from the islet chamber into the peritoneal cavity and/or the peritoneal cavity into the islet chamber thereby improving insulin transport and islet response. In one embodiment of the present invention, the device is implanted in the peritoneal cavity. Thus insulin would be secreted into blood and delivered systemically and insulin would be secreted into the portal system thereby delivering insulin directly to the liver. The advantage of such a dual secretion pathways ensures a better insulin/glucose control mechanism which in turn results in decreased side complications.

This novel mechanical artificial pancreas may be seeded or reseeded with the novel microbeads of the present invention in the following manner. By reseeding we mean that the mechanical device need not be surgically removed once it has lost its ability to produce insulin but fresh viable microbeads may be reinjected into said device alleviating the need for surgical removal.

The aforementioned mechanical artifical pancreas may be seeded with a solid gel or a slurry of gel microbeads. When seeded with solid gel, the pancreatic islet cells are suspended in liquid agar at about 40 degrees Celsius. Said agar/cell suspension is injected through the device's seeding ports. The device is thereafter allowed to cool below 37 degrees Celsius until the agar gels and forms an agar plug which fills the chamber. Said agar plug is advantageously stable because of the physical properties of agar, namely that it will not melt unless heated to over 80 degrees Celsius, an unlikely physiological event.

When seeded with a slurry of microbeads, the beads are directly injected into the seeding ports. Approximately 10–20 mL of packed beads are needed to seed the device.

If reseeding is desired, the chamber is first flushed with saline, approximately 150–300 mL, the beads removed and fresh beads injected. The beads are removed from the device by injecting saline into one port thereby flushing the beads out of the chamber through the opposite port. It takes approximately 150 to about 300 cc of saline to flush out greater than 90% of beads. Once the device is empty, it is reseeded in the same manner as the original seeding.

Since certain changes may be made without departing from the scope of the invention as described herein, it is intended that all matter described in the foregoing specification, including the examples, shall be interpreted as illustrative and not in a limiting sense.

We claim:

1. A method for producing agar microbead encapsulated cells comprising the steps of:
   a. suspending cells in a molten polysaccharide mixture of agarose and agaropectin to form a cell-agar mixture;
   b. emulsifying said cell-agar mixture in oil to form an emulsion of small liquid droplets suspended in oil;
   c. cooling said emulsion in oil to cause the droplets to gel and form gel microbeads made of the mixture of agarose and agaropectin; and
   d. collecting and washing the gel microbeads to produce the agar microbead encapsulated cells.

2. The method according to claim 1, wherein the cells are selected from the group consisting of pancreatic islet cells, hepatocytes, dopamine-secreting cells and hybridoma cells.

3. The method according to claim 1, wherein the cells are pancreatic islet cells.

4. The method according to claim 1, wherein the oil phase is selected from the group consisting of silicone fluid, vegetable oil and mineral oil.

5. A method for producing agar microbead encapsulated pancreatic islet cells comprising the steps of:
   a. suspending pancreatic islet cells in a molten mixture of agarose and agaropectin at a temperature of about 41 to about 43 degrees Celsius to form a cell-agar mixture;
   b. emulsifying said cell-agar mixture for about 10–30 minutes in an oil phase to form an emulsion of small liquid droplets suspended in the oil;
   c. cooling said emulsion in oil to cause the droplets to gel and form gel microbeads; and
   d. collecting and washing the gel microbeads to produce the agar microbead encapsulated cells.

6. The method according to claim 5, wherein saline or culture medium is added during the collecting and washing step.

7. The method according to claim 6, wherein the culture medium is selected from the group consisting of Minimal Essential Medium, Dulbecco's Modified Eagle Medium, Medium 199, Roswell Park Memorial Institute medium and Krebs/Ringers solution.

* * * * *